(12) United States Patent
Nardella (10) Patent No.: US 7,182,763 B2
(45) Date of Patent: Feb. 27, 2007

(54) WOUND CLOSURE DEVICE

(75) Inventor: Paul C. Nardella, Wareham, MA (US)

(73) Assignee: InstraSurgical, LLC, Hingham, MA (US)

( * ) Notice: Subject to any disclaimer, the term of this patent is extended or adjusted under 35 U.S.C. 154(b) by 182 days.

(21) Appl. No.: 10/995,648

(22) Filed: Nov. 23, 2004

(65) Prior Publication Data

US 2006/0111741 A1 May 25, 2006

(51) Int. Cl.
*A61B 18/14* (2006.01)

(52) U.S. Cl. .............................. 606/41; 606/49; 606/50

(58) Field of Classification Search .................. 606/48, 606/151, 219; 227/175.1
See application file for complete search history.

(56) References Cited

U.S. PATENT DOCUMENTS

| | | | |
|---|---|---|---|
| 5,201,900 A * | 4/1993 | Nardella | 606/157 |
| 5,207,691 A * | 5/1993 | Nardella | 606/142 |
| 5,665,085 A * | 9/1997 | Nardella | 606/41 |
| 5,674,231 A | 10/1997 | Green et al. | |
| 5,713,896 A * | 2/1998 | Nardella | 606/50 |
| 5,810,846 A | 9/1998 | Virnich et al. | |
| 5,817,091 A * | 10/1998 | Nardella et al. | 606/38 |
| 6,322,580 B1 * | 11/2001 | Kanner | 606/213 |
| 6,348,064 B1 | 2/2002 | Kanner | |
| 6,436,097 B1 * | 8/2002 | Nardella | 606/45 |
| 6,533,762 B2 | 3/2003 | Kanner et al. | |
| 6,565,582 B2 * | 5/2003 | Gifford et al. | 606/153 |
| 6,575,971 B2 * | 6/2003 | Hauck et al. | 606/52 |
| 2004/0254608 A1 * | 12/2004 | Huitema et al. | 606/219 |
| 2005/0159778 A1 * | 7/2005 | Heinrich et al. | 606/216 |

* cited by examiner

*Primary Examiner*—Michael Peffley
*Assistant Examiner*—Alex Toy
(74) *Attorney, Agent, or Firm*—Edwards Angell Palmer & Dodge LLP; Scott D. Wofsy (57) ABSTRACT

Disclosed is a wound closure device and method for using the same. The wound closure device includes a handle, a body portion extending distally from the handle, a stapling mechanism extending distally from the body portion and a mechanism for supplying electrical energy from an RF power supply to a fastener (e.g. staple) which is associated with the stapling mechanism. In a representative embodiment, the stapling mechanism includes an inner rod member disposed within an elongated outer sleeve and slidably movable therein. The rod member has an enlarged tip for deploying the fastener that is supported adjacent to the tip into body tissue. The wound closure device further includes an actuator mechanism associated with the handle and body portion and configured to facilitate relative movement of the inner rod and the outer sleeve so as to deploy the fastener into body tissue. In alternative embodiments, a second pole of the RF power supply is connected to a conductive ring associated with a vascular introducer.

18 Claims, 5 Drawing Sheets

WOUND CLOSURE DEVICE

BACKGROUND OF THE INVENTION

1. Field of the Invention

The present invention relates to wound closure devices for use during and after invasive medical procedures, and more particularly to, electrosurgical devices that include a stapler for closing a wound and an integrated mechanism which applies electrical energy to the body tissue within which the wound is formed to cauterize the wound site.

2. Background of the Related Art

The application of electrical energy to a surgical site for the purpose of cutting or cauterizing body tissue has been known for some time in the medical community and is generally referred to as either electrocautery and electrosurgery. Often "electrocautery" is used to describe "electrosurgery," but this is incorrect.

Electrocautery refers to applications wherein the electrical energy is supplied in a direct current, i.e., electrons flowing in one direction. In contrast, in electrosurgery an alternating current energy supply is used. Moreover, during electrocautery, current does not enter the patient's body, but flows though a wire or needle associated with the instrument and due to their impedance the wire/needle become very hot. The surgeon places the hot wire or needle in contact with body tissue so as to cut or cauterize the tissue.

In electrosurgery, the patient's body is included in the circuit. The circuit is composed of the generator, active electrode, patient, and patient return electrode. Pathways to ground are numerous but may include the operating room table, stirrups, staff members and equipment. Electrosurgery involves the cutting and/or coagulating of body tissue by application of high frequency electrical current.

In bipolar electrosurgery, the electrical current is applied through an electrode which contacts the body tissue to be treated. A return electrode is placed in contact with or in close proximity to the current-supplying electrode such that an electrical circuit is formed between the two electrodes. In this manner, the applied electrical current is limited to the body tissue positioned between the electrodes. The patient's tissue provides the impedance, producing heat as the electrons overcome the impedance. When the electrodes are sufficiently separated from one another, the electrical circuit is open and thus inadvertent contact of body tissue with either of the separated electrodes does not cause current to flow.

U.S. Pat. No. 5,573,534 to Stone, which is herein incorporated by reference in its entirety, discloses a bipolar surgical instrument for selectively grasping, manipulating, cutting and/or coagulating body tissue. To perform tissue cutting and/or coagulation, a high frequency power supply is connected to the bipolar instrument. Each electrode of the bipolar instrument is electrically isolated within the instrument and is separately connected to the high frequency power supply. Typical power supplies such as those available from Valleylab, Inc. of Boulder, Colo., are R.F. (i.e., radio frequency) generators which can produce different electrical waveforms to effect various electrosurgical procedures.

A waveform of continuous sinewaves alternating from positive to negative at the operating frequency of the R.F. generator is employed to cut tissue. Such a waveform creates short, intense electrical sparks to rapidly heat tissue; cells are exploded and the heat dissipated as steam. In contrast, a waveform consisting of pulsating sine waves alternating from positive to negative at the operating frequency of the R.F. generator is employed to coagulate tissue. Such a waveform creates longer, less intense sparks which heat tissue less rapidly, allowing heat to be dissipated more widely than during cutting. A combination of the cutting and coagulating waveforms produces the capability to cut tissue with enhanced hemostasis over the pure cutting waveform.

Due to its versatility and clinical effectiveness, monopolar is the most commonly used electrosurgical modality. In monopolar electrosurgery, the active electrode is in contact with the surgical site and the patient return electrode is somewhere else on the patient's body. The current passes through the patient as it completes the circuit from the active electrode to the patient return electrode.

U.S. Pat. Nos. 6,755,842 and 6,506,210, disclose advanced wound site management systems and methods. More specifically, these patents disclose a staple, stapler and introducer for closing a wound and for wound site management. The staple is deformable, and includes a plurality of tissue-piercing prongs which are expanded outwardly, inserted into tissue and collapsed inwardly to close the wound. The stapler includes a plurality of mechanisms to deform the staple into various positions. An introducer is provided that includes a plurality of spaced-apart wire guides for securing and centering the wound opening during a medical procedure, and during closure of the wound. The disclosures of U.S. Pat. Nos. 6,755,842 and 6,506,210 are herein incorporated by reference in their entirety.

A disadvantage of the wound site management systems disclosed in U.S. Pat. Nos. 6,755,842 and 6,506,210 and other prior art devices and systems is that they do not include an integrated cauterizing mechanism. As a result, a separate device must be used to cauterize the wound after the stapler and introducer have been removed. This not only adds complexity to the surgical procedure, but increases the time required for hemostasis.

In view of the above, there is a need for an improved wound closure device for use during and after invasive medical procedures which includes a stapler for closing the wound and an integrated mechanism for applying electrical energy to the body tissue in order to effect cauterization of the wound site.

SUMMARY OF THE INVENTION

The present invention relates to wound site management devices and methodologies for diagnostic and interventional procedures occurring at a wound site, for example, a puncture made in the wall of an artery or vein during a medical procedure. The puncture may be the result of a catheter-based intervention, although any puncture is contemplated, accidental or intentional. The present invention has particular utility for use in and around the femoral, radial, and brachial arteries after coronary/cardiac procedures. Other utilities include soft-tissue anchoring, tendon and artery joining, meniscal repair, thoracic lung closure, heart repair, endoscopic procedures, esophageal repair, laparoscopy, skin/epidermal wound closure and general tissue closure.

The present invention is further directed to a wound closure device which includes a handle, a body portion extending distally from the handle, a stapling mechanism extending distally from the body portion and a mechanism for supplying electrical energy from an RF power supply to a fastener (e.g. staple) which is associated with the stapling mechanism. The stapling mechanism includes an inner rod member disposed within an elongated outer sleeve and slidably movable therein. The rod member has an enlarged tip for deploying the fastener that is supported adjacent to the tip into body tissue. The wound closure device further includes an actuator mechanism associated with the handle and body portion and configured to facilitate relative movement of the inner rod and the outer sleeve so as to deploy the fastener into body tissue.

In a preferred embodiment, the actuation mechanism is operatively associated with a switch attached to the body portion of the closure device. When the actuation mechanism is activated, electrical energy is delivered to the fastener.

Preferably, a first electrical connector is provided on the body portion of the wound closure device which communicates electrical energy from a first pole of the RF generator to the fastener. Additionally, a second electrical connector can also be provided on the body portion of the wound closure device which communicates electrical energy from a second pole of the RF generator to the inner rod member. It is presently envisioned in such an embodiment, a non-conductive tube can be positioned over the inner rod member and within the outer sleeve so as to electrically isolate the rod from the sleeve. Alternatively, a non-conductive coating can be applied to the inner rod so as to electrically isolate the rod from the sleeve. Still further, preferably a portion of the fastener can be coated with parylene so as to electrically isolate the fastener from the flared tip of the rod member.

It is presently preferred that the electrical energy is delivered from the RF power supply to the fastener when the fastener is at least partially deployed into body tissue.

The present disclosure is also directed to a wound closure system which includes, among other elements, a surgical stapler and a vascular introducer. The surgical stapler has a handle, a body portion extending distally from the handle, and a stapling mechanism extending distally from the body portion of the closure device and including means associated with a distal tip thereof for deploying a fastener supported adjacent to the tip into body tissue.

The closure system further includes an actuation mechanism that is associated with the handle and body portion of the surgical stapler for and causing the stapling mechanism to deploy the fastener into body tissue when operated.

The vascular introducer includes an elongated outer sleeve formed of non-conductive material and an electrically conductive ring attached to a distal end of the sleeve. The electrically conductive ring is adapted to be electrically connected to a first pole of an RF power supply. In a preferred embodiment, the wound closure system further includes structure associated with the body portion of the closure device for electrically connecting the fastener to a second pole of the RF power supply.

In a still further embodiment, a guidewire is positioned within a central passage formed in the inner rod member. Preferably, the guidewire is electrically isolated from the inner rod member and electrically connected to a second pole of the RF generator.

The present disclosure is also directed to a method for closing a wound in a vessel which includes the steps of inserting a guidewire into a vessel lumen, placing a vascular introducer with a dilator over the guide wire and sliding a distal end of the dilator into the wound site so as to expand the wound site, and removing the guidewire and dilator from the wound site. The method further includes the steps of providing a surgical stapler which includes a distal tip portion having a staple supported thereby, means for electrically connecting the staple to a first pole of a RF power supply, and an actuator mechanism for deploying the staple, inserting the distal end of the surgical stapler into the introducer until the staple is adjacent to the vessel wall, operating the actuator mechanism of the stapling mechanism so as to deploy the staple, and providing electrical energy from a first pole of the RF power supply to the staple so as to cauterize the wound site.

In an alternative embodiment, the method can further include the steps of providing an electrically conductive ring attached to the introducer, connecting the ring to a second pole of the RF power supply and positioning the ring adjacent to the wound site when electrical energy is provided to the staple.

Still further, disclosed is a method for closing a wound in a vessel which includes the steps of inserting a tubular dilator into a wound site in a vessel, inserting a guidewire into the dilator and the vessel lumen, removing the tubular dilator from the wound site, placing a vascular introducer with a second dilator over the guide wire and sliding a distal end of the second dilator into the wound site so as to expand the wound site, and removing the guidewire and second dilator from the wound site. The method further includes the steps of providing a surgical stapler which includes a distal tip portion having a staple supported thereby, means for electrically connecting the staple to a RF power supply, and an actuator mechanism for deploying the staple, and the steps of inserting the distal end of the surgical stapler into the introducer until the staple is adjacent to the vessel wall, operating the actuator mechanism of the stapling mechanism so as to deploy the staple, and providing electrical energy from the RF power supply to the staple so as to cauterize the wound site.

It is envisioned that the disclosed method preferably includes the step of inserting stabilizing feet into the second dilator intraluminally and retracting the stabilizing feet until there is tactile feedback against the anterior wall of the artery. The stabilizing feet are shown in FIGS. 24A and 25A of U.S. Pat. No. 6,506,210 as well as in FIGS. 22A, 24A, 25A, 25, and 26 of U.S. Pat. No. 6,755,842.

These and other unique features of the system and method disclosed herein will become more readily apparent from the following description and accompanying drawings.

BRIEF DESCRIPTION OF THE DRAWINGS

So that those having ordinary skill in the art to which the disclosed system appertains will more readily understand how to make and use the same, reference may be had to the drawings wherein.

DETAILED DESCRIPTION OF PREFERRED EMBODIMENTS

Reference is now made to the accompanying figures for the purpose of describing, in detail, preferred and exemplary embodiments of the present disclosure. The figures and accompanying detailed description are provided to describe and illustrate exemplary manners in which the disclosed subject matter may be made and used, and are not intended to limit the scope thereof.

Figure 1:
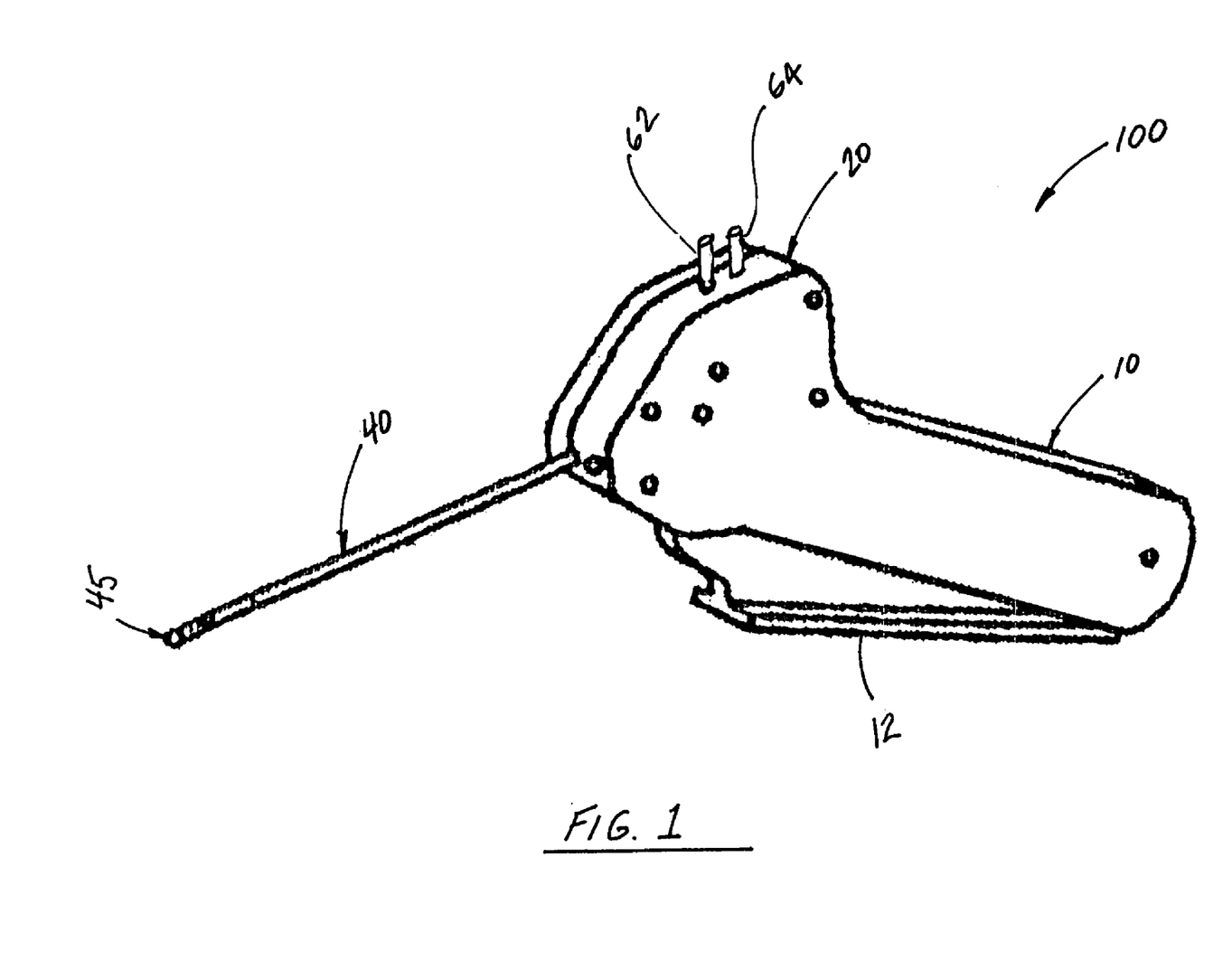
FIG. 1 is a perspective view of an embodiment of the wound closure device of the present invention.
Figure 3:
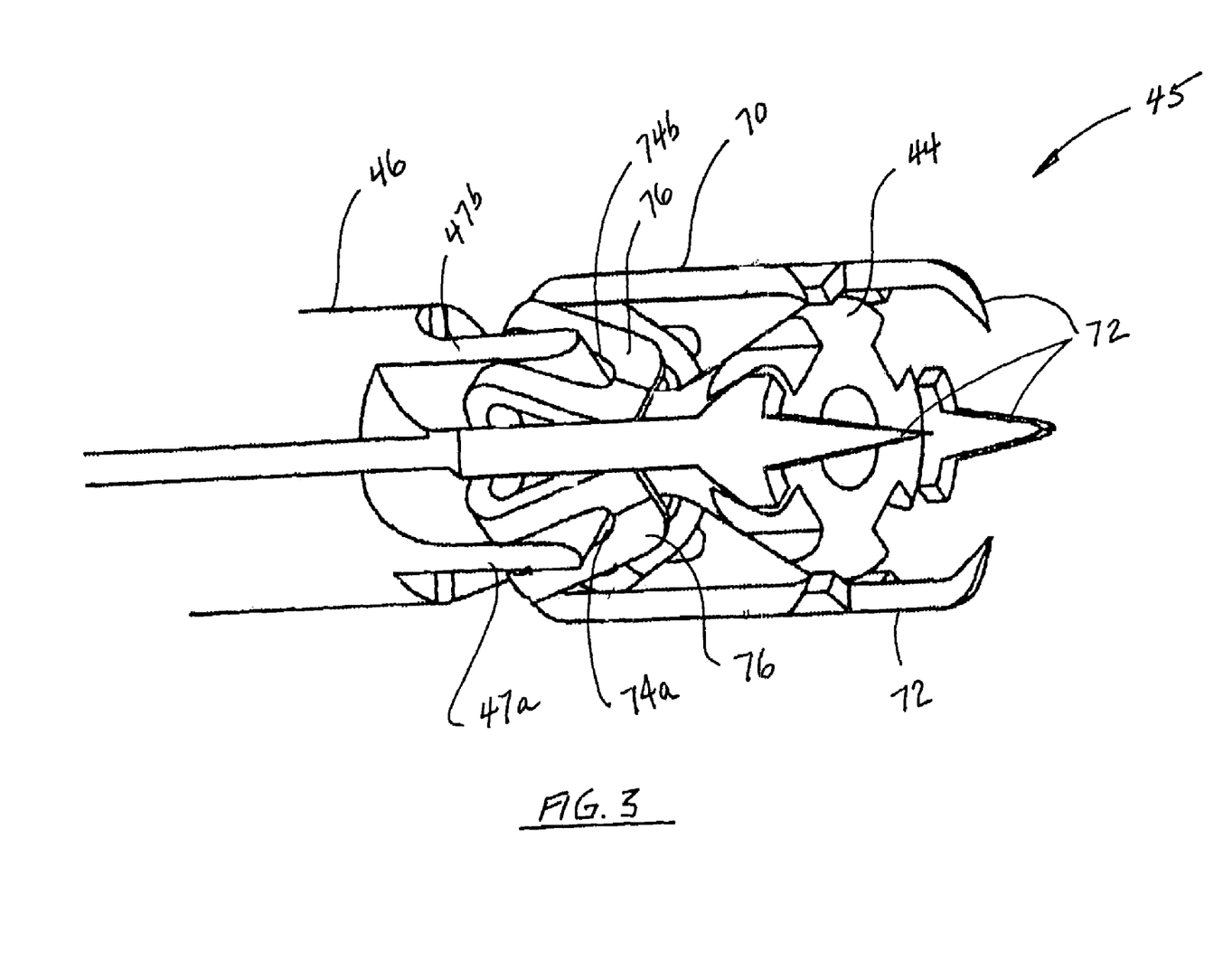
FIG. 3 is an enlarged perspective view of the distal end of the wound closure device of FIGS. 1 and 2.

Referring now to FIG. 1, there is illustrated a wound closure device constructed in accordance with an embodiment of the present invention and designated generally by reference number 100. Closure device 100 includes a handle 10, a main body section 20 posited at the distal end of the handle 10 and a stapling mechanism 40 extending distally from the main body section 20. The distal tip 45 of the stapling mechanism 40 is adapted for holding, forming and deploying a staple 70 (FIG. 3). An actuator mechanism 12 is associated with the handle portion 10 of the closure device 100 and causes the staple 70, or at least the tissue piercing portions 72 of the staple 70, to expand outwardly and then close about a wound as described in U.S. Pat. No. 6,755,842, which is herein incorporated by reference in its entirety.

Figure 2:
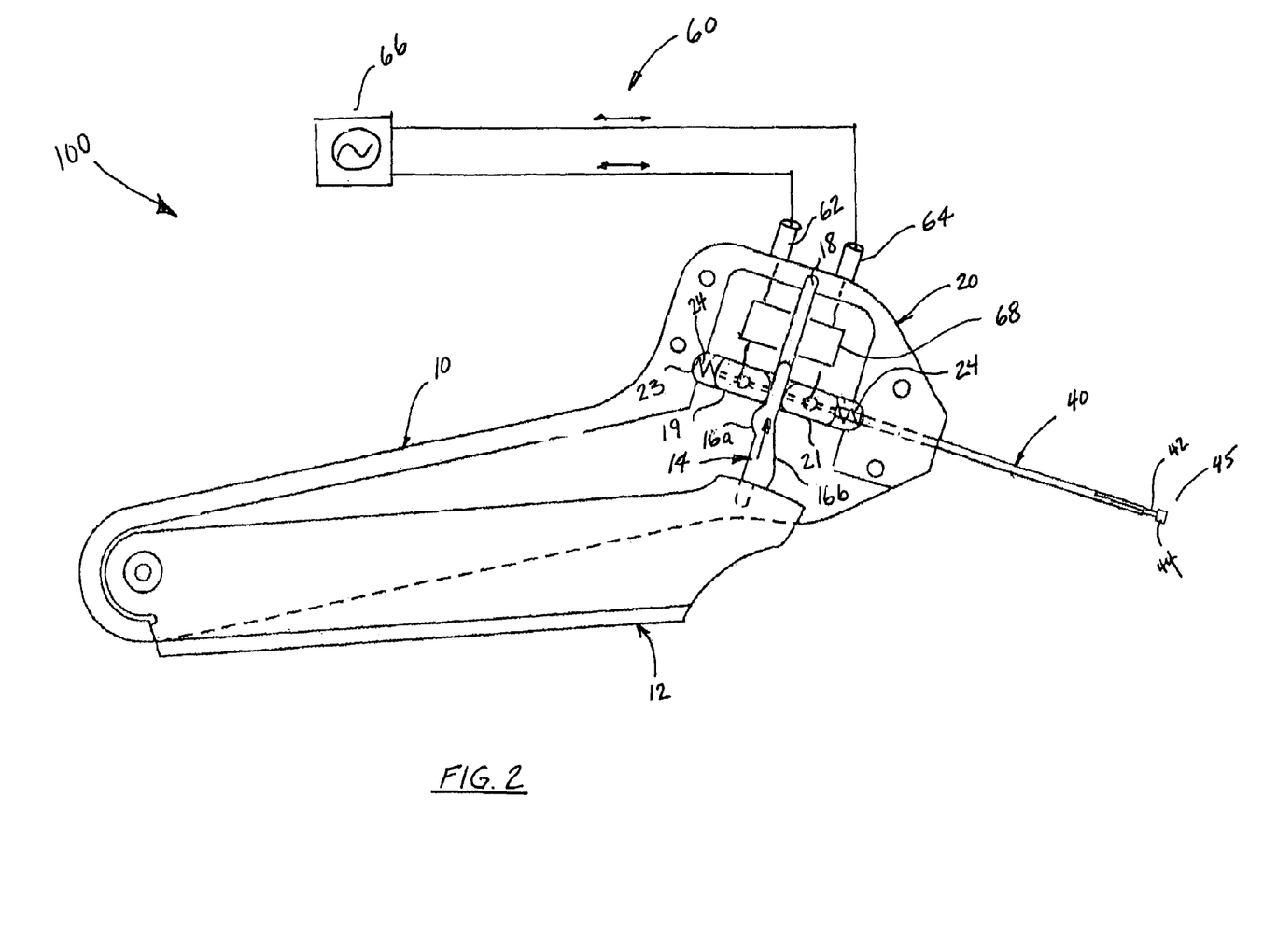
FIG. 2 is a side elevational view of the wound closure device of FIG. 1 illustrating an embodiment of the actuating mechanism for forming and applying a staple to the wound and an integrated bipolar cauterizing mechanism.

FIG. 2 depicts a side elevational view of closure device 100 and FIG. 3 provides a more detailed view of the distal tip 45 of stapling mechanism 40. The stapling mechanism 40 for closure device 100 is described in detail in U.S. Pat. No. 6,755,842, but for illustrative purposes, relevant portions of the operation of the stapling mechanism 40 will be described herein below. Those skilled in the art will readily appreciate that although the present invention is described below as being adapted for use with the stapler described in U.S. Pat. No. 6,755,842, the disclosed bipolar and monopolar cauterizing system and method can be integrated with other surgical staplers.

Referring again to FIGS. 2 and 3, the distal tip 45 of the stapling mechanism 40 preferably comprises an inner rod member 42 slidably disposed within outer sleeve 44. Rod 42 includes a flared or mandrel portion 44. Preferably, rod 42 is removable for staple attachment thereto, where a staple 70 is positioned between the mandrel 44 and the sleeve 46. The mandrel 44, as will be described below, is responsible for the forces generated on the staple 70.

The deployment of staple 70 can be summarized as follows. The staple 70 is placed as shown in FIG. 3 between the mandrel 44 and sleeve 46. Slots 74a–74d (74c and 74d not shown) in staple 70 engage axially projecting fingers 47a–d (47c and 47d not shown) of the sleeve 46. The prongs 72 of the staple 70 are dimensioned so as to fit over the mandrel 44, and tabs 76 (2 of 4 shown) are dimensioned so as to fit over the rod 42. The staple 70 engages both the mandrel 44 and sleeve 46. The staple 70 is urged into the first deformed position by the relative movement of the rod/mandrel 42/44 and the sleeve 46. As the mandrel 44 moves proximally, the tabs 76 of the staple 70 meet the narrowest part of the mandrel 44. Further movement forces the tabs 76 to move outwardly, causing the prongs 72 to likewise move outwardly. Once the tabs 76 clear the mandrel, outward movement of the tabs 76 and prongs 72 ceases. The movement of the mandrel 44 forces webs (not shown) to extend outwardly causing the prongs 72 to extend outwardly. Once the webs clear the mandrel 44, the outward movement of the prongs 72 ceases.

Figure 4:
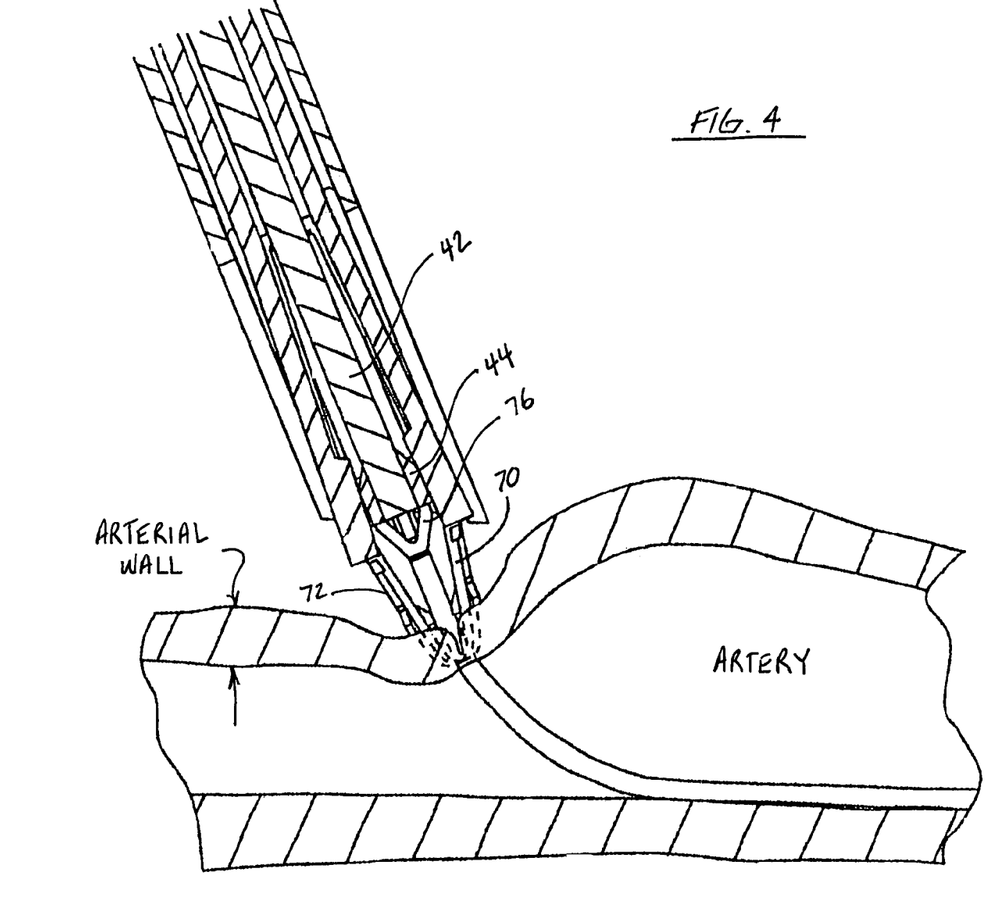
FIG. 4 is a side elevational view in cross section of a wound closure device of the present invention wherein the staple is fully deployed in the body tissue.

FIG. 4 depicts the final deployment of the staple 70 into the tissue or arterial wall. As the mandrel 44 is drawn further proximally and once the tabs 76 have cleared the mandrel 44, the shoulders (not shown) of the staple are spread outward, forcing the prongs 72 to move together (toward the centerline axis) and closing tissue therebetween.

As shown in FIG. 2, wound closure device 100 includes an integrated cauterizing system 60. The integrated cauterizing system 60 is adapted for applying electrical energy to the body tissue at the wound site in order to assist with hemostasis. Cauterizing system 60 includes an electrical generator 66, which in this embodiment is an RF generator that provides an alternating current energy supply. The main body section 20 of the closure device 100 has two standard electrical connectors associated therewith, namely connectors 62 and 64. The RF generator 66 has a first pole which is removably connected to electrical connector 62 and a second pole which is connected to electrical connector 64. These connectors 62/64 are electrically wired to the inner rod 42 and outer sleeve 46, respectively, through switch 68 and camming mechanism 14.

In the present embodiment, inner rod 42 and mandrel 44 are electrically isolated from the outer sleeve 46. One method for isolating the rod 42 and mandrel 44 from the sleeve 46 is to place a non-conductive tubing around elongated rod 42. Alternatively a non-conductive coating can be applied to the inner diameter of the sleeve 46 or the outer diameter of the rod 42. Those skilled in the art would readily appreciate that a variety of known methods exist for electrically isolating two conductive members from one another and alternative methods which are not described herein below can be used with departing from the inventive aspects of the present disclosure.

Referring now to FIG. 3, it is further intended that the staple 70, which is in contact with both the mandrel 44 and the sleeve 46 during forming and deployment, is electrically isolated from the mandrel 44, otherwise a short circuit will be created. One method for isolating the staple is to coat all of the surfaces of staple 70 which are in contact with the mandrel 44 with a non-conductive coating, such as parylene. However, the distal face of the mandrel 44 is uncoated. As a result, the sleeve 46 and the staple 70 will be electrically connected to one pole of the RF generator 66 and the mandrel 44 and rod 42 will be electrically connected to the other pole.

In the presently disclosed embodiment, the staple 70 and the mandrel 44 are only energized when staple prongs 72 have been expanded and at least partially inserted into the body tissue as shown in FIG. 4. Preferably this is accomplished by associating switch 68 with actuator mechanism 12 which controls the forming and deployment of staple 70. U.S. Pat. No. 6,755,842 discloses several actuator mechanism for deploying the staple and one of the embodiments is discussed hereinbelow with reference to FIG. 2 of the present disclosure. Those skilled in the art will readily appreciate that each of the actuator mechanism discussed in the '842 patent can be used with the present invention. Still further, although switch 68 is preferably associated with the actuator for the stapling mechanism, it can operated independently by the surgeon.

Actuator 12 includes a cam arm 14 which is urged in a direction indicated by the arrow to cause relative motion between the rod/mandrel 42/44 and the sleeve 46. Lobes 16A and 16B are located on opposite sides of cam 14. As the cam 14 is moved along slot 18, the lobe 16A urges a cam follower 19 in a linear motion along a slot 23. This urges the cam follower 19 proximally. The cam follower 19 is coupled to a mandrel rod 42. This deforms staple 70 in the second configuration. As the cam 14 is urged further, the cam follower 19 moves distally to stay in contact with the lobe 16A, which urges mandrel rod 42 distally. The same movement of the cam 14 urges lobe 16B to urge cam follower 21 distally. The cam follower 21 is coupled to a sleeve 46 and therefore, urges sleeve 46 distally. The downward slope of lobe 16A is parallel with upward slope of lobe 16B so the mandrel rod 42 and the sleeve 46 move distally in unison and the staple 70 is advanced into the tissue. The movement of the cam follower 19 down the slope of lobe 16A then ceases while the movement of cam follower 21 continues up the slope of lobe 16B, the staple 70 is deformed into the closed or deployed configuration. It is at this point that switch 68 is activated and energizes the cauterizing system 60. The switch can be activated manually or automatically. One method for activating the switch automatically can include providing a third lobe on cam 14 which contacts the switch 66.

Springs 24 can be provided to return cam followers 19 and 21, respectively, to an initial position. Of course an additional spring can be provided in slot 18 to move cam 14 back to an original position.

Those skilled in the art would readily appreciate that although the presently disclosed embodiment depicts a biopolar electrosurgical system and method for cauterizing the body tissue, the system can be monpolar. In such an embodiment, preferably the outer sleeve 46 of the stapling mechanism 40 would be connected to the RF generator and function as the active electrode in the system. Alternatively, for example, the inner rod 42 and mandrel 44 could be connected to the RF generator and function as the active electrode. As described supra, in a monopolar system the active electrode is positioned at the surgical site and a return pad/electrode is attached to the patient at another location. The current flows from the active electrode through the wound site and through the patient to the return electrode.

Figure 5:
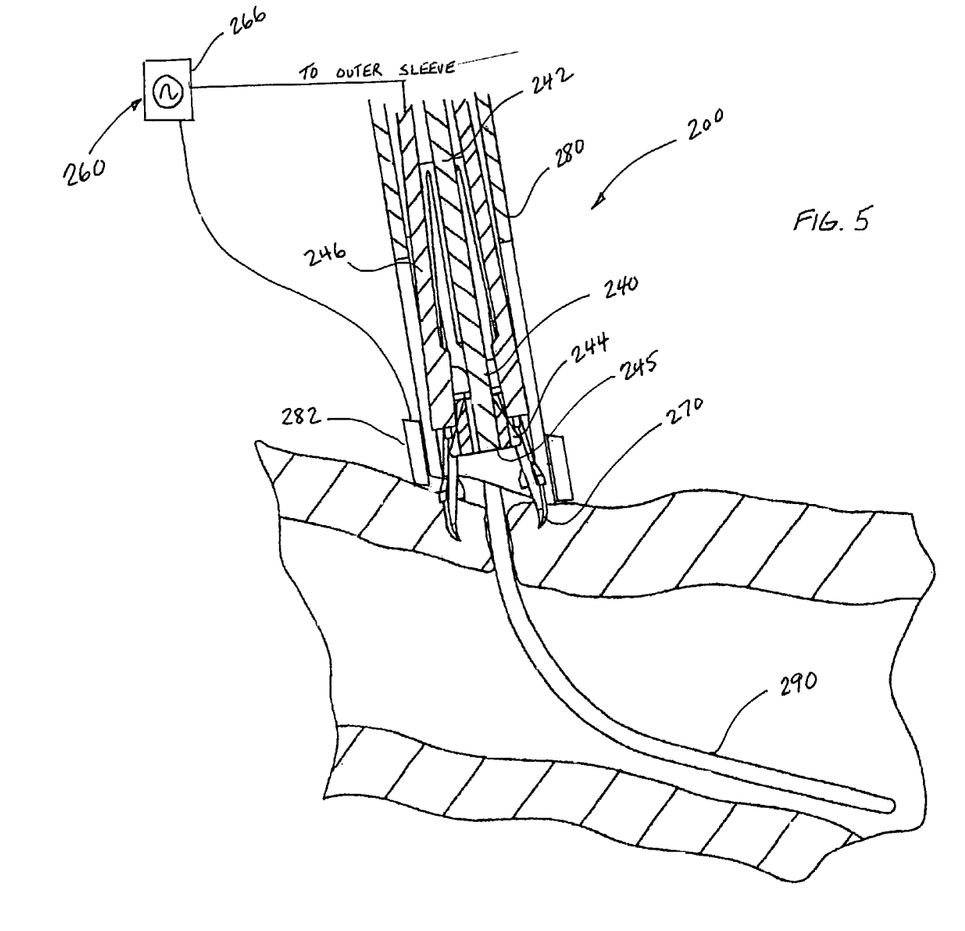
FIG. 5 is a cross sectional view of an alternative embodiment of the wound closure device of the present invention having a return electrode associated with a vascular introducer.

Referring now to FIG. 5 which depicts an alternative embodiment of the wound closure of the present invention designated generally by reference number 200. As shown in this figure, a vascular introducer has been used in the surgical procedure and the introducer sheath 280 and guidewire 290 are still inserted into the body cavity. Wound closure device 200 has been properly positioned at the wound site by using the sheath 280 and the guidewire 290 as described in U.S. Pat. No. 6,755,842.

Similarly to the previously described embodiments, wound closure device 200 includes a stapling mechanism 240 having a distal tip portion 245 which is adapted and configured for forming and inserting a staple 270 into body tissue. Wound closure device 200 also includes a cauterizing mechanism 260 which uses electrical energy to assist with hemostasis of the wound site. Cauterizing mechanism 260 has a first pole of the RF generator 266 electrically connected to preferably the outer sleeve 246 of the closure device or alternatively, for example, the rod/mandrel 242/246 so as to create an active electrode and to electrify the staple 270. However, unlike the previously described embodiments, the RF generator 266 of cauterizing mechanism 260 has a second pole electrically connected to an electrically conductive ring 282 which is associated with introducer sheath 280. In such an embodiment, the electrical current travels over a path that includes the RF generator 266, the outer sleeve 246 of closure device 200, the staple 270, the wound site, and the conductive ring 282.

Skilled artisans in the field would recognize that the first pole of the RF generator can be connected to the guidewire(s) 290 in lieu of the outer sleeve 246 of the stapling mechanism 240. In such an embodiment, the guidewire(s) 290 which is/are positioned within an axial passage formed in the rod/mandrel 242/244 would be insulated from the rod/mandrel 242/244. Preferably, the guidewire(s) 290 would have a non-conductive external coating which extends over most of its length as is known to those skilled in the art. In such an embodiment, current flows over a path that includes the generator 266, the guide wire 290, the wound site and the conductive ring 282 associated with the introducer 280.

An exemplary method for deploying the wound closure device of the present disclosure can be described as follows. Following a completed medical procedure, such as angioplasty, typically a small tubular dilator extends from the wound site through the skin of the patient. A tubular dilator is shown in FIG. 20A of U.S. Pat. No. 6,506,210 and in FIG. 20A of U.S. Pat. No. 6,755,842. Two dilators are also shown in FIGS. 18–20 of U.S. Pat. No. 6,506,210 and in FIGS. 18–20 of U.S. Pat. No. 6,755,842. To start the wound closure procedure, a guidewire is inserted into the dilator and extends through the wound site into the artery. The tubular dilator is then removed and a vascular introducer (with dilator) is placed over the guide wire and inserted into the vascular opening so as to stretch the wound site. The introducer is inserted until brisk bleeding is noted from the dilator port, making the depth of the arterial lumen. The guidewire is then removed and shortly thereafter the dilator is also removed. In alternative embodiments, prior to removal of the dilator, stabilizing feet are inserted into the dilator and deployed intraluminally and retracted until there is tactile feedback against the anterior wall of the artery. The stabilizing feet are shown in FIGS. 24A and 25A of U.S. Pat. No. 6,506,210 as well as in FIGS. 22A, 24A, 25A, 25, and 26 of U.S. Pat. No. 6,755,842.

The distal end of the closure device which includes the stapling mechanism is then inserted into the introducer until the prongs of the staple are positioned adjacent to the vessel wall. Then the actuator mechanism is engaged and deploys the staple while simultaneously switching on and off the cauterizing mechanism.

Those skilled in the art would readily appreciate that although the presently disclosed embodiment depicts a biopolar electrosurgical system and method for cauterizing the body tissue, the system can be monpolar. In such an embodiment, preferably the conductive ring 282 associated with the introducer sheath 280 would be connected to the RF generator and function as the active electrode in the system. Alternatively, for example, guidewire 290 could be connected to the RF generator and function as the active electrode. As described supra, in a monopolar system the active electrode is positioned at the surgical site and a return pad/electrode is attached to the patient at another location. The current flows from the active electrode through the wound site and through the patient to the return electrode.

What is claimed is:

1. A wound closure device comprising:
   a) a handle;
   b) a body portion extending distally from the handle;
   c) a stapling mechanism extending distally from the body portion and including an inner rod member disposed within an elongated outer sleeve and slidably movable therein, the rod member including an enlarged tip for deploying a fastener supported adjacent the tip into body tissue, wherein a portion of the fastener is provided with an insulative coating so as to electrically isolate the fastener from the enlarged tip of the rod member;
   d) an actuation mechanism associated with the handle and body portion and configured to facilitate relative movement of the inner rod and the outer sleeve so as to deploy the fastener into body tissue; and e) means associated with the body portion of the closure device for electrically connecting the fastener to a RF power supply.

2. The closure device as recited in claim 1, wherein the actuation mechanism is operatively associated with a switch attached to the body portion of the closure device, wherein electrical energy is delivered to the fastener when the actuation mechanism is operated.

3. The closure device as recited in claim 1, further comprising a first electrical connector provided on the body portion of the wound closure device which communicates electrical energy from a first pole of a RF generator to the fastener.

4. The closure device of claim 3, further comprising a second electrical connector provided on the body portion of the wound closure device which communicates electrical energy from a second pole of a RF generator to the inner rod member.

5. The closure device of claim 1, further comprising a non-conductive tube positioned over the inner rod member and within the outer sleeve so as to electrically isolate the rod from the sleeve.

6. The closure device of claim 1, further comprising a non-conductive coating applied to the inner rod so as to electrically isolate the rod from the sleeve.

7. The closure device of claim 1, wherein a portion of the fastener is coated with parylene so as to electrically isolate the fastener from the enlarged tip of the rod member.

8. The closure device of claim 1, wherein electrical energy is delivered to the fastener when the fastener is at least partially deployed into body tissue.

9. A wound closure system comprising:
a) surgical stapler including;
  i) a handle;
  ii) a body portion extending distally from the handle;
  iii) a stapling mechanism extending distally from the body portion of the closure device and including means associated with a distal tip thereof for deploying a fastener supported adjacent to the tip into body tissue;
  iv) an actuation mechanism associated with the handle and body portion of the surgical stapler for and causing the stapling mechanism to deploy the fastener into body tissue when operated; and
b) a vascular introducer which includes an elongated outer sleeve formed of non-conductive material and an electrically conductive ring attached to a distal end of the sleeve; wherein the electrically conductive ring is adapted to be electrically connected to a first pole of an RF power supply.

10. A wound closure system as recited in claim 9, further comprising means associated with the body portion of the closure device for electrically connecting the fastener to a second pole of the RF power supply.

11. A wound closure device a recited in claim 10, wherein the stapling mechanism includes an inner rod member disposed within an elongated outer sleeve and slidably movable therein; the rod member including an enlarged tip for deploying the fastener into body tissue.

12. A wound closure device a recited in claim 11, wherein the outer sleeve is electrically connected to the second pole of the RF power supply and communicates electrical energy to the fastener.

13. The closure device of claim 12, wherein electrical energy is delivered to the fastener when the fastener is at least partially deployed into body tissue.

14. A wound closure device as recited in claim 11, wherein a guidewire is positioned within a central passage formed in the inner rod member, the guidewire being electrically isolated from the inner rod member and electrically connected to a second pole of the RF generator.

15. A method for closing a wound in a vessel, comprising the steps of:
a) inserting a guidewire into a vessel lumen;
b) placing a vascular introducer with a dilator over the guide wire and sliding a distal end of the dilator into the wound site so as to expand the wound site;
c) removing the guidewire and dilator from the wound site;
d) providing a surgical stapler which includes a distal tip portion having a staple supported thereby, means for electrically connecting the staple to a first pole of a RF power supply, and an actuator mechanism for deploying the staple;
e) inserting the distal end of the surgical stapler into the introducer until the staple is adjacent to the vessel wall;
f) operating the actuator mechanism of the stapling mechanism so as to deploy the staple; and
g) providing electrical energy from a first pole of the RF power supply to the staple so as to cauterize the wound site.

16. The method as recited in claim 15, further comprising the steps of:
a) providing an electrically conductive ring attached to the introducer;
b) connecting the ring to a second pole of the RF power supply; and
c) positioning the ring adjacent to the wound site when electrical energy is provided to the staple.

17. A method for closing a wound in a vessel, comprising the steps of:
a) inserting a tubular dilator into a wound site in a vessel;
b) inserting a guidewire into the dilator and the vessel lumen; removing
c) the tubular dilator from the wound site
d) placing a vascular introducer with a second dilator over the guide wire and sliding a distal end of the second dilator into the wound site so as to expand the wound site;
e) removing the guidewire and second dilator from the wound site;
f) providing a surgical stapler which includes a distal tip portion having a staple supported thereby, means for electrically connecting the staple to a RF power supply, and an actuator mechanism for deploying the staple;
g) inserting the distal end of the surgical stapler into the introducer until the staple is adjacent to the vessel wall;
h) operating the actuator mechanism of the stapling mechanism so as to deploy the staple; and
i) providing electrical energy from the RF power supply to the staple so as to cauterize the wound site.

18. The method as recited in claim 17, further comprising the steps of inserting stabilizing feet into the second dilator intraluminally and retracting the stabilizing feet until there is tactile feedback against the anterior wall of the artery.

* * * * *